US006926685B1

(12) United States Patent
Modglin

(10) Patent No.: US 6,926,685 B1
(45) Date of Patent: Aug. 9, 2005

(54) STRAP SYSTEM

(75) Inventor: Michael D. Modglin, Braselton, GA (US)

(73) Assignee: DeRoyal Industries, Inc., Powell, TN (US)

(*) Notice: Subject to any disclaimer, the term of this patent is extended or adjusted under 35 U.S.C. 154(b) by 55 days.

(21) Appl. No.: 10/395,527

(22) Filed: Mar. 21, 2003

(51) Int. Cl.[7] .................................................. A61F 5/00
(52) U.S. Cl. ........................................ 602/5; 602/19
(58) Field of Search ............................... 128/845, 846, 128/869, 870; 602/19, 5

(56) References Cited

U.S. PATENT DOCUMENTS

| | | | |
|---|---|---|---|
| 2,828,737 A | * | 4/1958 | Hale .......................... 602/19 |
| 4,005,506 A | | 2/1977 | Moore |
| 5,658,244 A | | 8/1997 | Townsend et al. |
| 5,911,697 A | * | 6/1999 | Biedermann ................. 602/19 |
| 6,363,936 B1 | * | 4/2002 | McCormick ................ 128/870 |
| 6,610,022 B1 | * | 8/2003 | Ashbaugh |
| 2002/0029406 A1 | | 3/2002 | Meyer |

FOREIGN PATENT DOCUMENTS

WO    WO 00/78168 A1    12/2000

* cited by examiner

Primary Examiner—Michael A. Brown
(74) Attorney, Agent, or Firm—Luedeka Neely & Graham, PC

(57) ABSTRACT

A strap system for use with a brace of the type having a first shell generally conforming to a first body part of a user and a second shell generally conforming to a second body part of the user. The strap system includes a first strap and a first buckle located on the first strap, a second strap and a second buckle located on the second strap, a plurality of slides securable to the second shell for receiving the straps, a first latch member securable to a first portion of the first shell, and a second latch member securable to a second portion of the first shell.

10 Claims, 7 Drawing Sheets

STRAP SYSTEM

FIELD OF THE INVENTION

This invention relates generally to securement straps. More particularly, this invention relates to a strap system that is particularly useful for securing medical braces about the human anatomy.

BACKGROUND AND SUMMARY OF THE INVENTION

Conventional securement devices, especially strap systems for medical braces, desire improvement. One type of medical brace is a bi-valve spinal brace having a pair of substantially rigid shells. The shells are positioned in an overlapping relationship, with one shell surrounding the back of the user and the other surrounding the front of the torso of the user. A plurality of straps are riveted to the shells and are used to secure the shells in place. This type of strap system is inconvenient to use and desires improvement.

In a preferred embodiment, the invention relates to a strap system for use with a brace of the type having a first shell generally conforming to a first body part of a user and a second shell generally conforming to a second body part of the user.

In a preferred embodiment, the strap system includes a first strap and a first buckle located on the first strap, a second strap and a second buckle located on the second strap, a plurality of slides securable to the second shell for receiving the straps, a first latch member securable to a first portion of the first shell, and a second latch member securable to a second portion of the first shell.

In another aspect, the invention relates to a strap system for use with a brace of the type having a shell generally conforming to a body part of a user.

In a preferred embodiment, the strap system includes a strap and a buckle located on the strap, a pair of slides securable to a first portion of the shell for receiving the strap, and a latch member securable to a second portion of the shell.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

FIG. 7 is a perspective view of a strap system in accordance with another embodiment of the invention.

DETAILED DESCRIPTION

Figure 1:
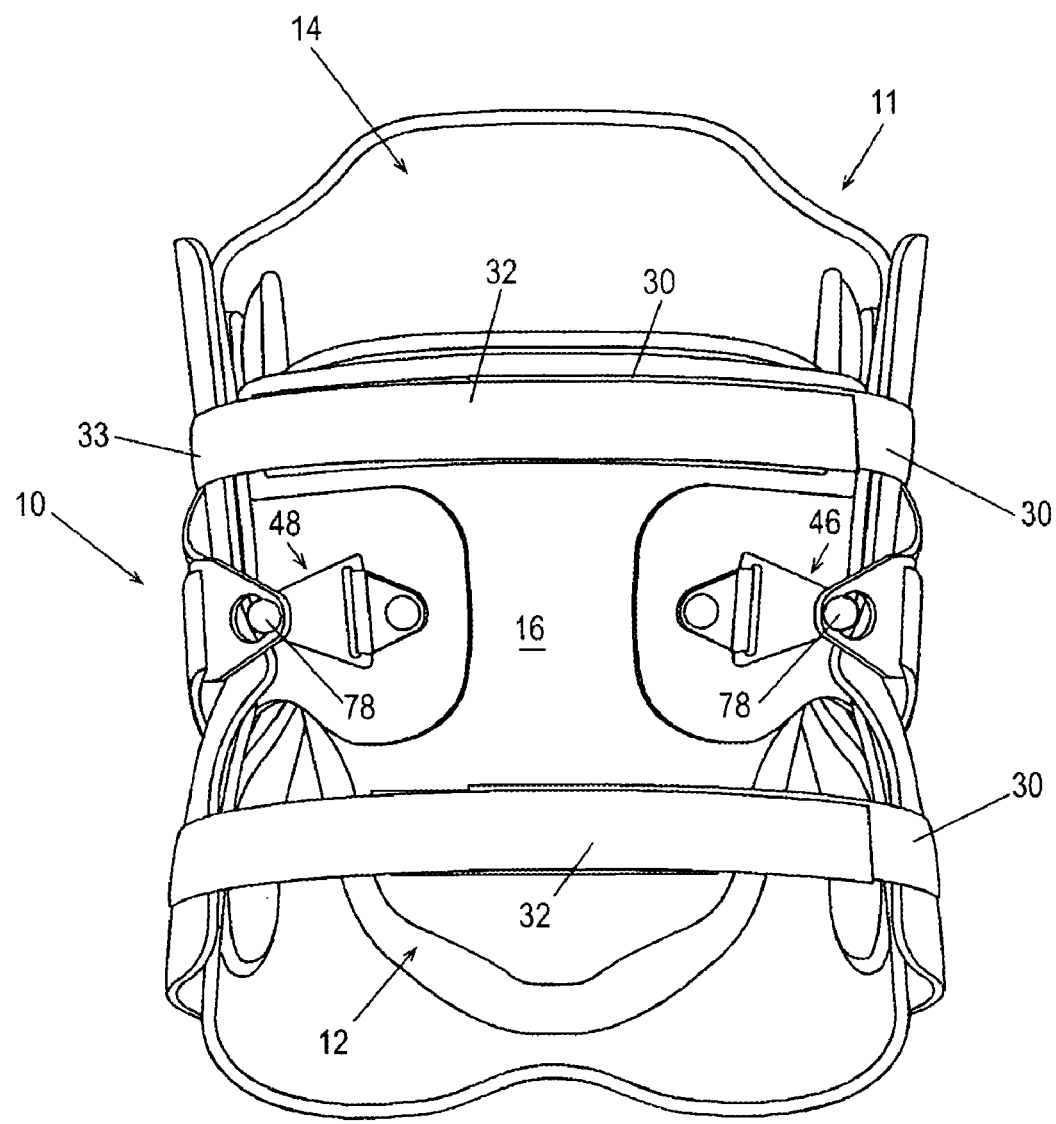
FIG. 1 is a front perspective view of a spinal brace utilizing a strap system in accordance with a preferred embodiment of the invention.
Figure 2:
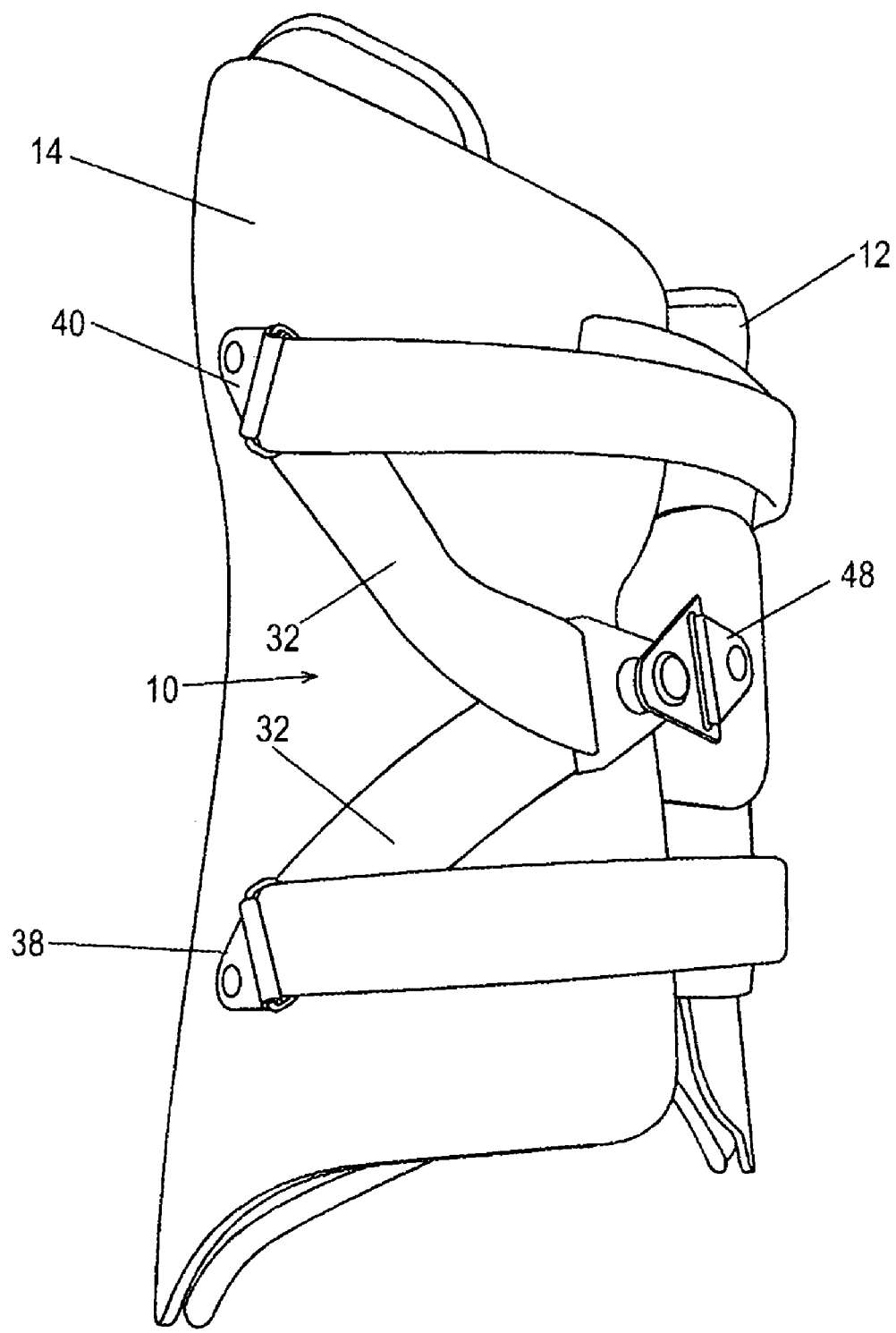
FIG. 2 is a side view of the brace and strap system of FIG. 1.
Figure 3:
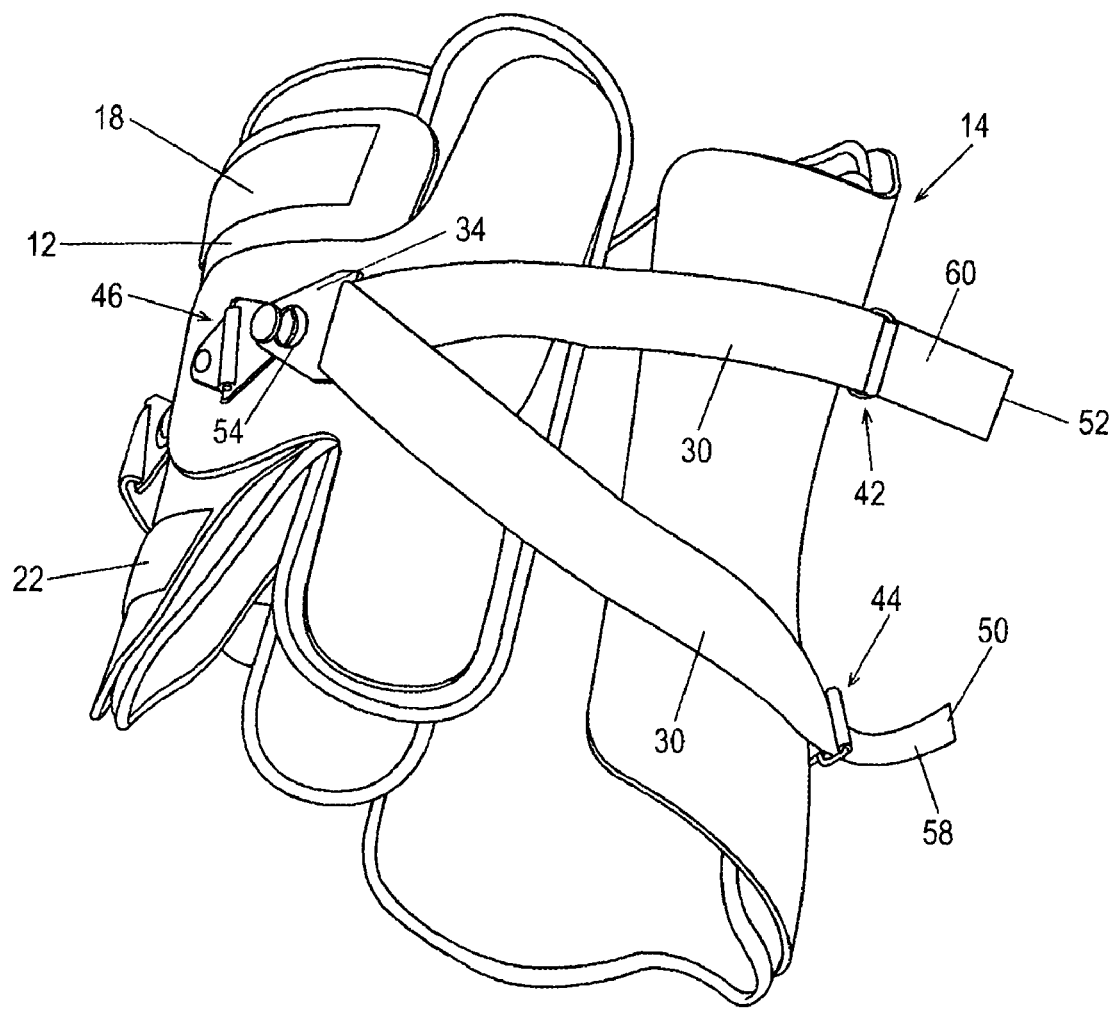
FIG. 3 is an exploded view of the brace and strap system of FIG. 1.
Figure 4:
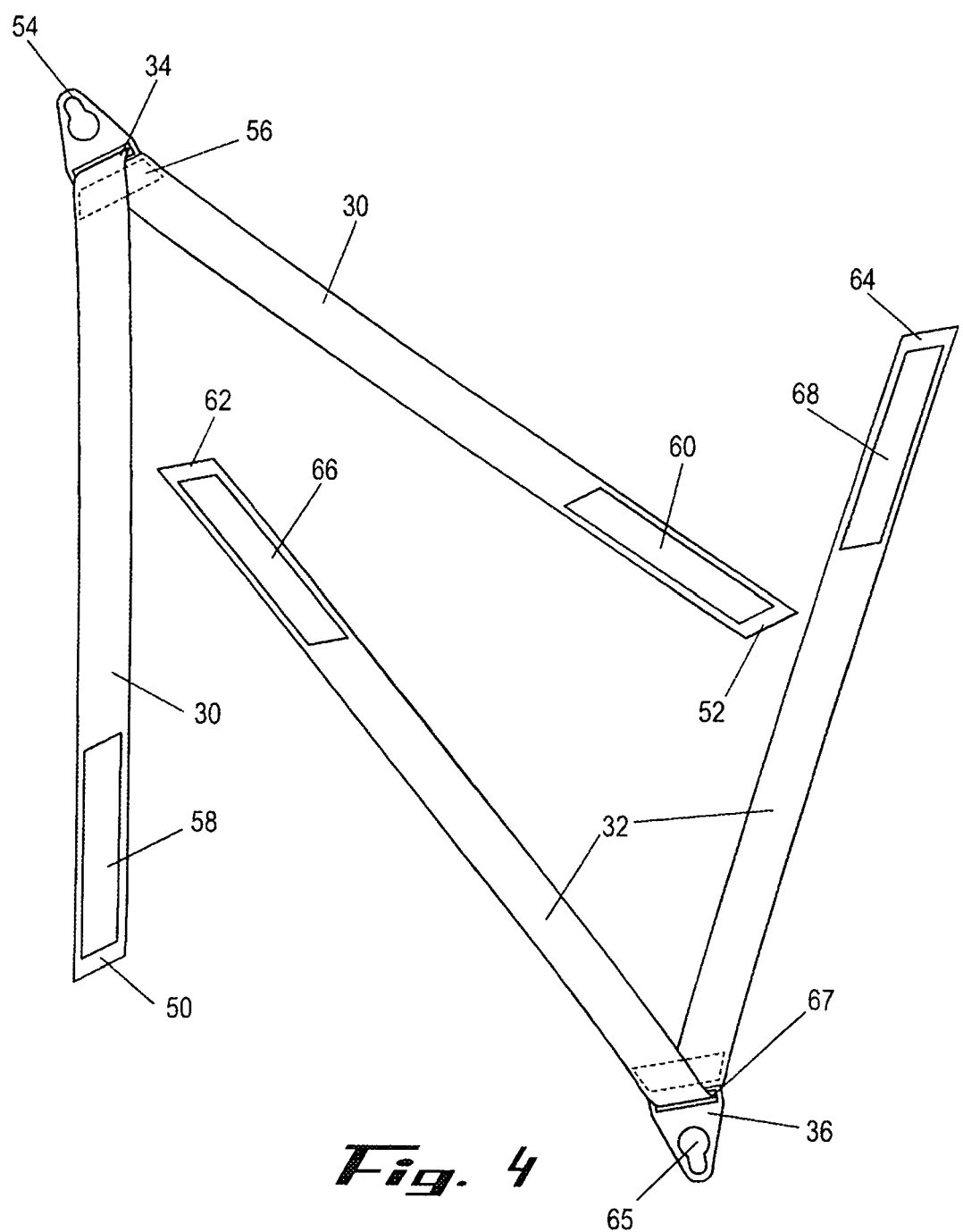
FIG. 4 is a plan view of strap components of a strap system in accordance with a preferred embodiment of the invention.
Figure 5:
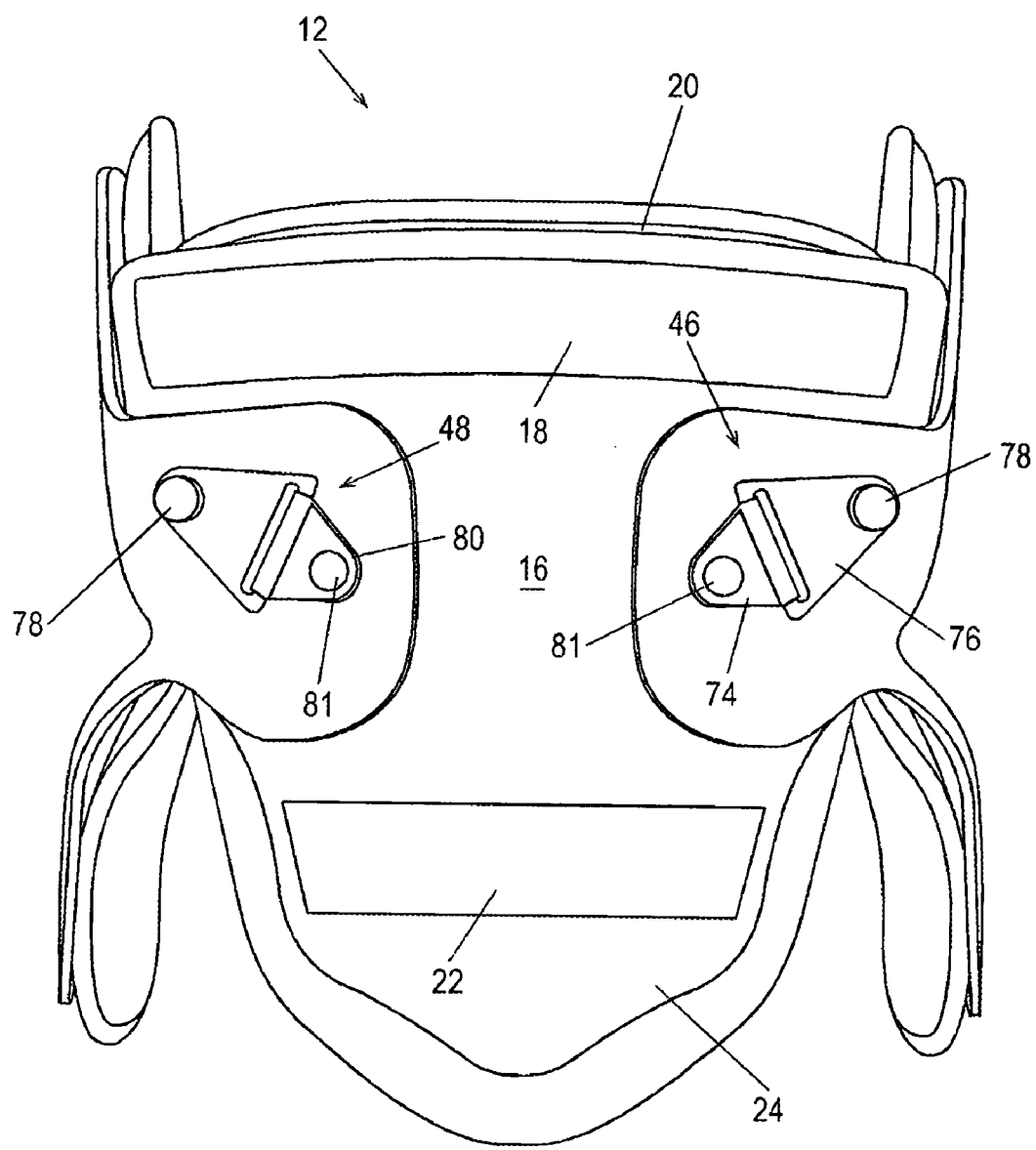
FIG. 5 is an exterior view of a front shell of the brace of FIG. 1 which shows components of the strap system attached to the front shell.
Figure 6:
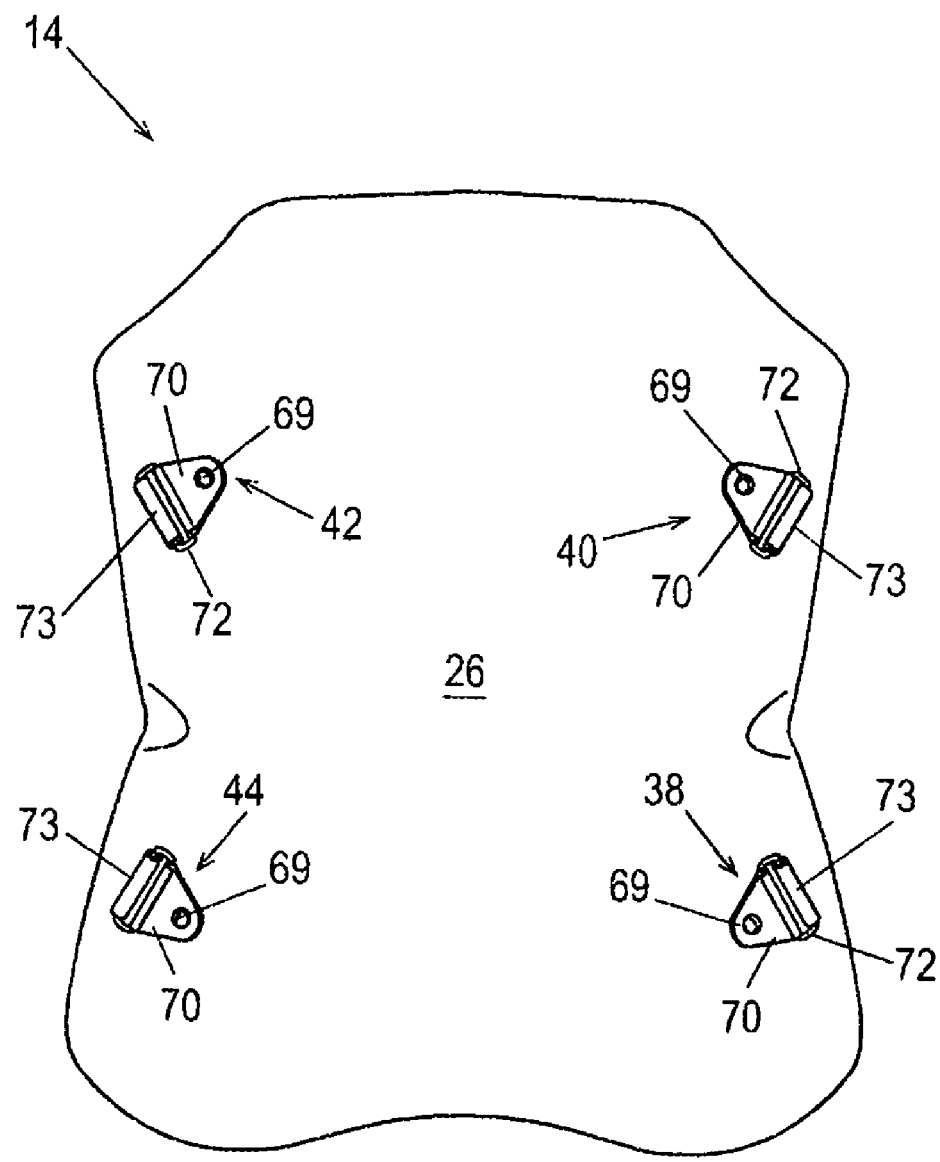
FIG. 6 is an exterior view of a rear shell of the brace of FIG. 1 which shows components of the strap system ached to the rear shell.
Figure 1:
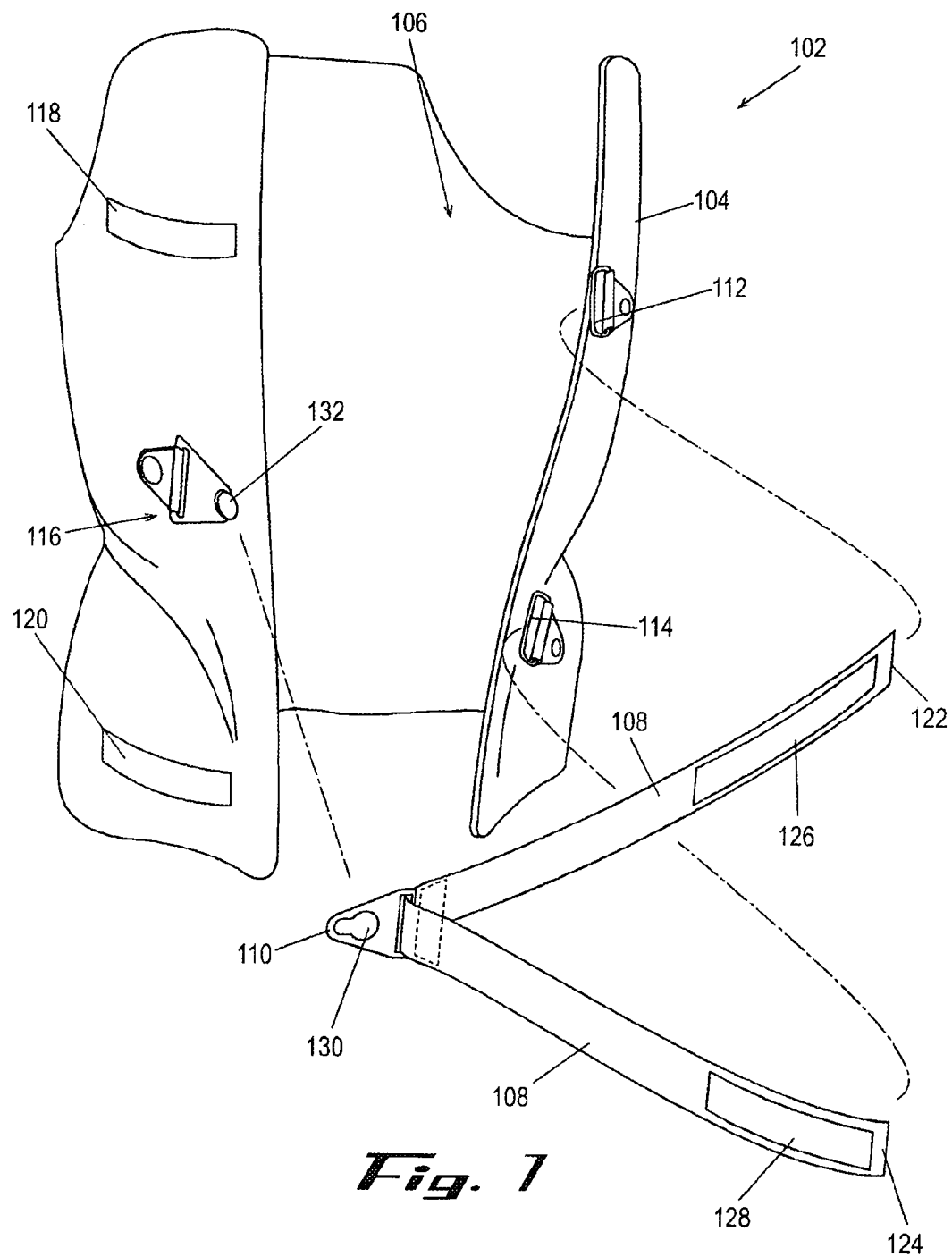

With initial reference to the drawings, the invention relates to a strap system 10. For the purpose of example, the strap system 10 is shown for use with a spinal brace 11 having a front shell 12, and a rear shell 14. The brace 11 has shells 12 and 14 configured to serve as a lumbar-sacral orthosis (LSO). It will be understood, however, that the strap system 10 may be used with a variety of braces as well as in other applications. It is noted that the shells described herein are generally rigid shells of the type used for spinal braces. It will be understood that the shells could also be relatively flexible and of other than plastic construction, such as cotton or other fabric used for wrist braces and the like.

The depicted brace 11 is the subject of commonly assigned and co-pending application Ser. No. 10/395,763, entitled SPINAL BRACE, filed Mar. 21, 2003, incorporated herein by reference in its entirety.

The font shell 12 is of molded thermoplastic construction and includes an exterior surface 16. An elongate strip of material 18 having an outer surface configured of a loop or hook material of the type suitable for releasably engaging a hook material or loop material respectively is preferably secured, as by adhesive, substantially laterally across the exterior 16 surface of the shell 12 adjacent a first edge 20 thereof.

Likewise, an elongate strip of material 22 having an outer surface configured of a loop (or hook) material of the type suitable for releasably engaging a hook (or loop) material is preferably secured, as by adhesive, substantially laterally across the exterior surface adjacent a second edge 24. Alternatively, other attachment devices such as stitches, buttons, fasteners, and the like may be used.

The rear shell 14 is preferably made of the same material as the front shell 12 and preferably configured to partially overlap the front shell 12 when installed on a user. The shell 14 includes an exterior surface 26.

The strap system 10 includes a pair of straps 30 and 32, and a pair of buckles 34 and 36 fixedly secured on the straps 30 and 32. Slides 38, 40, 42, and 44 are attached to the exterior surface 26 of the rear shell 14, and latch members 46 and 48 are attached to side portions of the shell 12.

The strap 30 includes opposite ends 50 and 52 and has a suitable length which may preferably range from about 38 to about 48 inches for use with the spinal brace 11, although other lengths may likewise be suitable. The buckle 34 is preferably of one-piece plastic construction and includes a latching aperture 54 and a mounting slit 56. The strap 30 is passed through the slit 56 and the buckle 34 positioned at about the midpoint of the strap 30. The strap 30 is folded about itself and preferably secured, as by stitches or other fastening devices, to form the strap in a generally A-shape, with the buckle 34 fixedly located at the apex. A hook material 58 is preferably provided on the strap 30 adjacent the end 50 and a hook material 60 is preferably provided on the strap 30 adjacent the end 52.

The strap 32 is preferably identical to the strap 30 and is identically configured with regard to the buckle 36 and includes ends 62 and 64 and hook material 66 and 68. The buckle 36 is identical to the buckle 34, and likewise includes aperture 65 and a mounting slit 67.

The slides 38–44 are configured for receiving and slidably retaining the straps and are mountable to the shell 14 as by fasteners such as rivets 69 or the like. As will be seen, each slide 38–44 includes a mounting base 70 and an elongate loop 72 pivotally mounted to the base 70 and configured for passage of the straps 30 or 32 there through. A plastic cylinder 73 is preferably mounted on the loop 72 to serve as a roller to facilitate sliding of the straps. The internal diameter of the cylinder 73 is preferably larger than the diameter of the loop 72 so that the cylinder turns freely.

The latch members 46 and 48 each include a base 74 for mounting to the shell 12 and a latch 76 pivotally mounted to the base 74. The latch 76 is configured for releasably engaging the latching apertures 54 of the buckles 34 and 36, and preferably includes a mushroom-shaped projection 78 for releasably engaging the latching apertures 54 of the buckles.

The base 74 preferably includes an aperture 80 for passage of a fastener to secure the base to the exterior surface of the shell, such as threaded fastener 81. The fastener 81 may pass through an aperture provided through the shell and threadably engage a flanged threaded cylinder located adjacent the opposite surface of the shell.

The strap system 10 is utilized to secure the brace 11 in place after it is positioned on a user. The brace 11 is generally installed around the trunk of a user by placing the front shell 12 adjacent the front of the user and the rear shell adjacent the spine of the user, with the sides of the rear shell 14 overlapping the sides portion of the front shell 12. The buckles of the straps, such as buckle 34 of the strap 32, are secured to the latch members, such as latch member 48, as by engaging the latching aperture 48 around the projection 78. Also, the straps are passed through the slides, as by passing ends 50 and 52 through the slides 42 and 44.

The shells 12 and 14 may be urged toward one another as desired by pulling on the ends of each of the straps to place the ends adjacent the strips of loop material 48 and 50. The hook material associated with the ends of the straps is then matingly engaged with the loop material 18 and 22 attached to the exterior of the shell 12. As will be appreciated, the ends of the straps may be overlapped, as the exterior surfaces of the strap provide a loop material engageable with the hook material. Also, the location of the hook and loop material may be interchanged and/or other releasable fastening devices, such as snaps, buckles, and the like may be used to maintain the ends of the straps in place.

The strap system 10 is easier to use than conventional strap systems, and enables a user to conveniently secure a brace in place. The strap system 10 is also easily adjusted by a user to enable enhanced comfort benefits.

Turning now to FIG. 7, there is shown a strap system 100 for use with a brace 102 having a shell 104. The shell 104 includes a slit 106 that enables the brace to be positioned around a body part of a user. The strap system 100 includes a strap 108, and buckle 110 fixedly secured on the strap 108. Slides 112 and 114 are attached to the exterior surface the rear shell 104, and a latch member 116 is attached to the shell 104. A pair of strips of loop (or hook) material 118 and 120 are attached to the shell 104, preferably on the same side of the slit 106 as the buckle 110.

The strap 108 is preferably substantially identical to the strap 30 and includes a pair of opposite ends 122 and 124, with hook material 126 and 128 located thereon adjacent the ends. The buckle 110 is preferably substantially identical to the buckle 34 and includes a latching aperture 130. The slides 112 and 114 are preferably substantially identical to the slides 38–44. The latch member 116 is preferably substantially identical to the latch member 46 and includes a projection for 132 for releasably engaging the latching aperture 130. The slides 112 and 114 and the latch member 116 are preferably secured to the shell 104 in a manner similar to that previously described for the latch member 46 and the slides 38–44.

The strap system 100 may be used in a manner similar to that described for the strap system 10. For example, the shell 104 is placed around a body part and the strap system 100 is used to maintain it in position and otherwise urge the shell against the body part. The ends 122 and 124 of the strap 108 are placed through the slides 112 and 114 and the buckle 110 engaged with the latch member 116. The ends 122 and 124 are then pulled to impart tension and placed in engagement with the hook material 118 and 120.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A brace, comprising a first shell generally conforming to a first body part of a user, a second shell generally conforming to a second body part of the user, and a strap system for securing the shells in fitting engagement with the body parts of the user, wherein the strap system includes a first strap and a first buckle located on the first strap, a second strap and a second buckle located on the second strap, a plurality of slides secured to the second shell for receiving the straps, a first latch member secured to a first portion of the first shell, and a second latch member secured to a second portion of the first shell.

2. The brace of claim 1, wherein the first buckle is secured to the first strap and the second buckle is secured to the second strap.

3. The brace of claim 1, wherein the plurality of slides comprises a first pair of slides for receiving the first strap and a second pair of slides for receiving the second strap.

4. The brace of claim 1, wherein the first buckle includes a latching aperture and the first latch member includes a projection for releasably engaging the latching aperture.

5. The brace of claim 1, wherein the buckle includes a latching aperture and the latch member includes a projection for releasably engaging the latching aperture.

6. A brace, comprising a shell having a slit and generally conforming to a body part of a user and a strap system for securing the shell in fitting engagement with the body part of the user, wherein the strap system includes a strap and a buckle located on the strap between the opposite ends of the strap, a pair of slides secured to a first portion of the shell on one side of the slit for receiving the strap, and a latch member secured to a second portion of the shell on the opposite side of the slit and positioned for engaging the buckle such that the brace may be urged against the body part by pulling on the strap.

7. The brace of claim 6, wherein the buckle is secured to the strap.

8. The strap system of claim 6, wherein the buckle is secured to the strap.

9. The strap system of claim 6, wherein the buckle includes a latching aperture and the latch member includes a projection for releasably engaging the latching aperture.

10. A strap system for use with a brace of the type having a shell including a slit and generally conforming to a body part of a user, the strap system comprising a strap and a buckle located on the strap between the opposite ends of the strap, a pair of slides securable to a first portion of the shell on one side of the slit for receiving the strap, and a latch member securable to a second portion of the shell on the opposite side of the slit and positionable for engagement with the buckle such that the brace may be urged against the body part by pulling on the strap.

* * * * *